US011435460B2

(12) United States Patent
Dhatt

(10) Patent No.: US 11,435,460 B2
(45) Date of Patent: Sep. 6, 2022

(54) ULTRASOUND IMAGING SYSTEM WITH STYLE TRANSFER IMAGE ENHANCEMENT

(71) Applicant: FUJIFILM SonoSite, Inc., Bothell, WA (US)

(72) Inventor: Davin Dhatt, Woodinville, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 49 days.

(21) Appl. No.: 15/973,010

(22) Filed: May 7, 2018

(65) Prior Publication Data
US 2019/0339371 A1 Nov. 7, 2019

(51) Int. Cl.
G01S 7/52 (2006.01)
G01S 15/89 (2006.01)
A61B 8/00 (2006.01)
G06K 9/62 (2022.01)
G06V 20/00 (2022.01)
(Continued)

(52) U.S. Cl.
CPC .......... *G01S 7/52053* (2013.01); *A61B 8/463* (2013.01); *G01S 7/52046* (2013.01); *G01S 15/8911* (2013.01); *G06K 9/6256* (2013.01); *G06V 20/00* (2022.01); A61B 8/5269 (2013.01);
(Continued)

(58) Field of Classification Search
CPC ........ G01S 7/52; G01S 15/89; G01S 7/52046; G01S 15/8906; G01S 7/52053; G01S 7/52084; G01S 15/8911; G01S 7/52073; A61B 8/00; A61B 8/5215; A61B 8/463; A61B 8/5269; G06K 9/00; G06K 9/62; G06K 9/4628; G06K 9/6271;
(Continued)

(56) References Cited

U.S. PATENT DOCUMENTS 6,714,667 B1 * 3/2004 Mooney ................. A61B 8/467
382/128
9,373,059 B1 * 6/2016 Heifets ..................... G06T 1/60
(Continued)

FOREIGN PATENT DOCUMENTS

EP 2434454 3/2012
JP 2016-154858 9/2016
(Continued)

OTHER PUBLICATIONS

International Preliminary Search Report and Written Opinion on the Patentability of Application No. PCT/US2019/030479, dated Nov. 19, 2020, 10 pages.
(Continued)

Primary Examiner — Isam A Alsomiri
Assistant Examiner — Amie M Ndure
(74) Attorney, Agent, or Firm — Womble Bond Dickinson (US) LLP

(57) ABSTRACT

An ultrasound imaging system enhances the display of an ultrasound image by applying a selected style to the content of the ultrasound image. The style may be of anatomic illustrations of a particular anatomical feature such as tissue type or may be the style of a previously obtained ultrasound image that shows tissue well. The style of other imaging modes can also be applied. In some embodiments, a training mode of the ultrasound imaging system implements a style transfer technique to enhance the appearance of captured ultrasound image data.

19 Claims, 4 Drawing Sheets

(51) Int. Cl.
  *A61B 8/08* (2006.01)
  *G06F 3/04845* (2022.01)
  *G06F 3/0482* (2013.01)

(52) U.S. Cl.
  CPC ........ *G06F 3/0482* (2013.01); *G06F 3/04845* (2013.01)

(58) Field of Classification Search
  CPC ............. G06K 9/6256; G06K 9/00624; G06K 2209/05; G06F 3/0482; G06F 3/04845
  See application file for complete search history.

(56) References Cited

U.S. PATENT DOCUMENTS

| | | | | |
|---|---|---|---|---|
| 9,589,374 | B1* | 3/2017 | Gao | G06T 11/008 |
| 9,730,643 | B2* | 8/2017 | Georgescu | G16H 50/30 |
| 10,675,004 | B2* | 6/2020 | Lundberg | A61B 8/0841 |
| 2004/0064043 | A1* | 4/2004 | Rielly | G01S 7/52038 600/437 |
| 2004/0073112 | A1* | 4/2004 | Azuma | A61B 8/467 600/437 |
| 2004/0118210 | A1* | 6/2004 | Tooma | B06B 1/06 73/625 |
| 2004/0127796 | A1* | 7/2004 | Chalana | A61B 8/4455 600/449 |
| 2005/0100208 | A1 | 5/2005 | Suzuki et al. | |
| 2014/0058266 | A1 | 2/2014 | Call et al. | |
| 2015/0025372 | A1* | 1/2015 | Ghosh | A61B 6/032 600/431 |
| 2015/0238148 | A1* | 8/2015 | Georgescu | G06K 9/4628 600/408 |
| 2016/0125605 | A1* | 5/2016 | Lee | A61B 8/085 382/131 |
| 2016/0128672 | A1* | 5/2016 | Kim | G06F 16/5862 600/437 |
| 2016/0350620 | A1* | 12/2016 | Rao | G06K 9/6256 |
| 2018/0021022 | A1* | 1/2018 | Lundberg | G01S 7/52085 600/424 |

FOREIGN PATENT DOCUMENTS

| | | |
|---|---|---|
| JP | 2016154858 | 9/2016 |
| WO | 2018048575 A1 | 3/2018 |
| WO | 2018-127498 | 7/2018 |
| WO | 2018127498 | 7/2018 |

OTHER PUBLICATIONS

International Search Report for Application No. PCT/US2019/030479, dated Aug. 16, 2019, 14 pages.
International Search Report for Application No. PCT/US2019/030479 dated Aug. 16, 2019, 16 pages.
Gatys, L.A., Ecker, AS., Bethge, M.: A neural algorithm of artistic style (2015).
Johnson, J., Alahi, A, Li, F.: Perceptual Losses for Real-Time Style Transfer and Super-Resolution (2016).
Extended European Search Report on the Patentability of Application No. 1980052.6-1206/3790470 PCT/US2019030479 dated Dec. 17, 2021, 9 pages.

* cited by examiner

ULTRASOUND IMAGING SYSTEM WITH STYLE TRANSFER IMAGE ENHANCEMENT

TECHNICAL FIELD

The disclosed technology relates to ultrasound imaging systems and in particular to systems for enhancing the appearance of ultrasound image features.

BACKGROUND

Ultrasound imaging is becoming an increasingly used imaging modality due to its relative low cost and non-ionizing radiation. With ultrasound imaging, a transducer directs ultrasonic sound waves into a region of interest and receives the corresponding echo signals. Signal processing circuitry in an imaging system combines the electronic echo signals produced by the transducer elements and produces indications of a characteristic of the combined signals such as its magnitude, phase shift, power, harmonic content or other characteristics that are quantified into image pixel data for display to the user.

Ultrasound images can often include speckle or reverberation artifacts that appear in an image but do not represent tissue structures. In addition, because ultrasound is not an optical imaging modality, it requires a certain level of training to learn how tissue structures in an ultrasound image will appear. The technology disclosed herein relates to systems to improve the appearance of tissue structures in ultrasound images.

SUMMARY

To address the above-mentioned problems and others, the disclosed technology relates to an ultrasound imaging system that produces images of tissue in a region of interest. A processor in the imaging system is configured to display an ultrasound image in a style that makes the tissue or other anatomical features in the image more easily recognized. In one embodiment, ultrasound image data is processed by a neural network that is trained to produce data for an image in a selected style. In some embodiments, the ultrasound system stores more than one trained neural network where each neural network is trained to apply a particular style to an input ultrasound image. A processor selects the neural network corresponding to a style that is to be applied to an ultrasound image.

The style applied to an ultrasound image can correspond to, for example, the style of an anatomical illustration, the style of a photograph of the particular type of anatomy or anatomical feature, the style of another type of imaging modality (e.g. MRI, CT scan) or the style of a previously acquired ultrasound image. The particular style applied to an ultrasound image can be selected in a number of ways such as by the user, by the type of examination being performed, by the imaging mode of the ultrasound system, or by the type of transducer being used etc.

DETAILED DESCRIPTION

Figure 1:
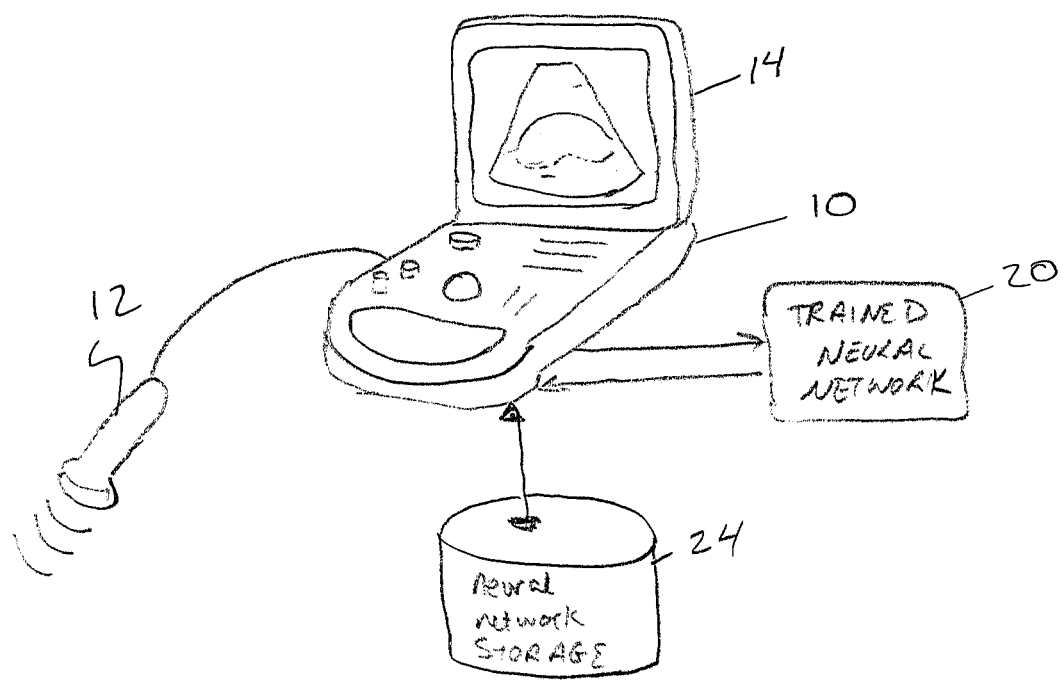
FIG. 1 shows a representative ultrasound imaging system for implementing the disclosed technology.

To improve the appearance of features such as tissue, organs, blood or the like in ultrasound images, an ultrasound imaging system of the disclosed technology uses one or more processors to apply a selected style to an ultrasound image in a different style and to display the style-transferred image to the user. FIG. 1 shows a representative ultrasound imaging system 10 that may be a hand-held, portable or cart-based imaging system. The system 10 includes a transducer 12 that generates ultrasound energy, directs the energy into a region of interest and receives the corresponding reflected echo signals. The transducer 12 converts the received acoustic energy of the echo signals into corresponding electrical signals that are processed by circuitry in the transducer or the imaging system 10 including, but not limited to, analog to digital converters, circuitry for amplification, filtering, beamforming and digital signal processing. Image processing circuitry converts the processed ultrasound signals into pixel data that can be displayed on one or more video monitors 14. The ultrasound system 10 also includes a number of controls with which a user can interact with and use the imaging system such as buttons, knobs, a keyboard, keypad, a trackball, a trackpad, touch wheel, touch screen or the like.

To improve the ability of less experienced ultrasound users to recognize anatomical features such as tissue, fluids (e.g. blood) or organs in an ultrasound image, the disclosed technology enhances the appearance of such features by changing the style with which the ultrasound data are displayed. Although the following description is primarily directed to improving the appearance of organs in an ultrasound image, it will be appreciated that the disclosed technology can be used with all these anatomical feature types. In one embodiment, a user can select one of several different styles they would like to apply to an ultrasound image to be displayed. One or more processors (e.g. CPU, GPU, DSP or a combination thereof) or pre-configured logic circuitry (e.g. FPGA, ASIC or the like) in the ultrasound imaging system provides ultrasound image data for a region of interest to a trained neural network that applies a selected style to the input ultrasound image data. An image that blends the content of the input ultrasound image with the selected style is displayed to the user so that the features in the ultrasound image are more recognizable. The user can view the style blended image, the original ultrasound image or both on a video monitor. The style blended image can be stored along with the unmodified ultrasound image or sent to a remote computer system via wired or wireless communication link.

Figure 2B:
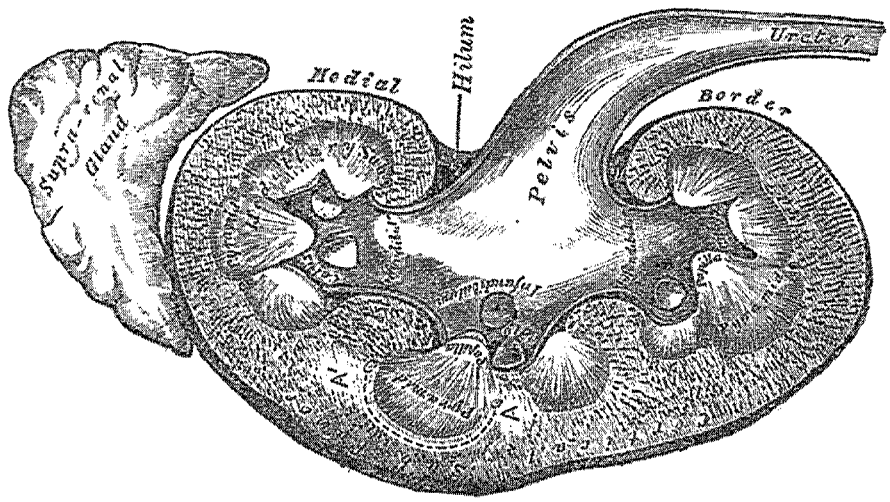
FIG. 2B shows an image of a kidney from Gray's Anatomy.
Figure 2A:
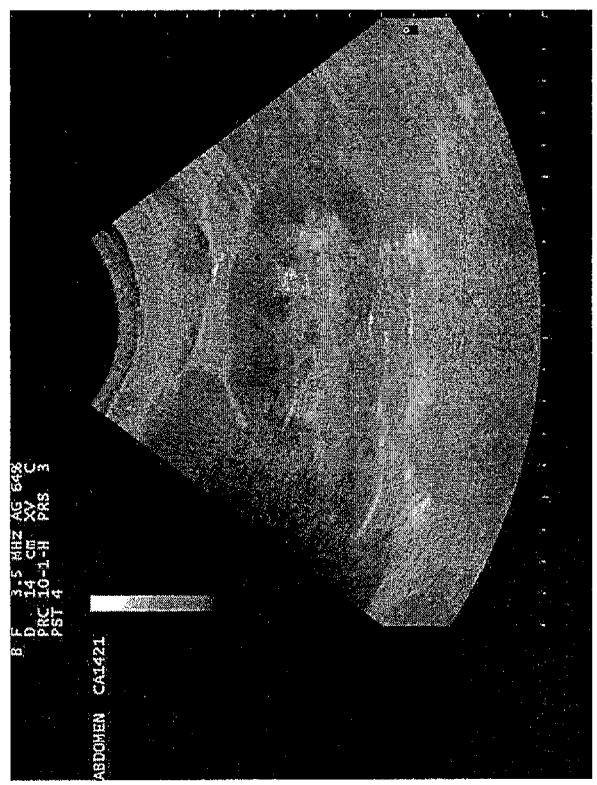
FIG. 2A shows a representative ultrasound image of a human kidney.

FIG. 2A shows a representative ultrasound image of a human kidney. To an inexperienced ultrasound technician, the image may not be immediately recognizable as kidney tissue. FIG. 2B shows a classic image of a kidney from a 1918 version of Gray's Anatomy. To improve the appearance of the tissue or other features (e.g. blood, bone, ligaments, etc.) in an ultrasound image, the ultrasound imaging system of the disclosed technology includes one or more processors that are programmed or are configured to display the ultrasound image data in the style of a more conventional anatomical illustration or another style. For example, the processor of the ultrasound imaging system is programmed to display the ultrasound image shown in FIG. 2A in the classic Gray's Anatomy style using a trained neural network for style blending. In one embodiment, the style blending operations can be used in a training mode to improve the appearance of tissue in ultrasound images. The style blending feature can be turned on and off so that the operator of the ultrasound imaging system can view the ultrasound image data with and without the style blending enhancements.

Figure 3:
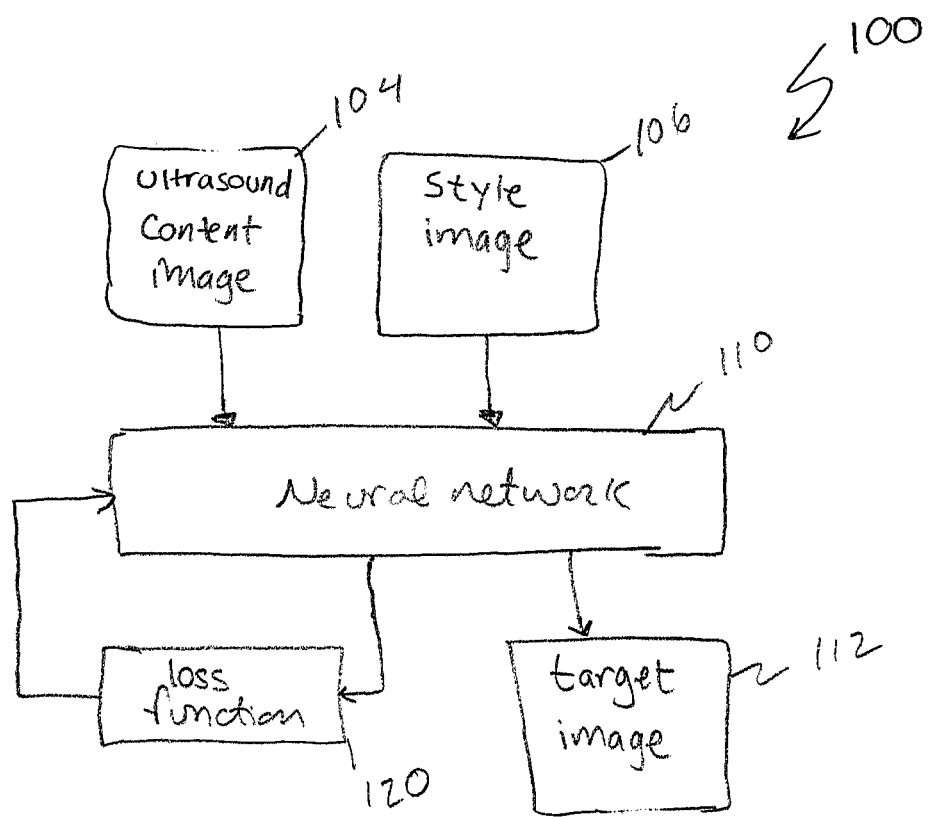
FIG. 3 is a block diagram of a system for training a neural network to apply a selected style to an ultrasound image in accordance with one embodiment of the disclosed technology.

FIG. 3 shows a block diagram of one embodiment of a system 100 for training a neural network to enhance the appearance of an ultrasound image by applying a different style to the image. In the embodiment shown, the system 100 receives an ultrasound image. Typically, the ultrasound image is a B-mode image but could be an image in other modalities such as a Doppler image, M-mode image, Color Flow image etc. As described herein, the ultrasound image is called the ultrasound content image 104. A style image 106 is an image whose style should be blended with the content image 104 or used a guide for displaying the content image 104. A neural network 110 such a convolutional neural network (e.g. VGG or a similar available neural network) is trained to produce a target image 112 in the style of the style image 106 but retains the content of the content image 104. In some embodiments, one or more processors that train the neural network 110 calculate a loss function 120 that quantifies the differences in content between the target image 112 and the content image 104 and the differences in style between the target image 112 and the style image 106 as a function of a number of coefficients, weights and bias values used by the neural network 110. The processors execute an optimization algorithm, such as a gradient descent method, that computes changes to the coefficients, weights and bias values that are fed back into the neural network 110 so that both the differences in content and style are lessoned. This process continues until either the error is minimized or for a predetermined number of iterations.

In one embodiment, a user is allowed to provide their own style image that is used to train the neural network 110. In some embodiments, the style image is an anatomical image in a particular style like the Gray's Anatomy image shown in FIG. 2B. However, other well-known depictions of tissue from, for example, a medical text book could be used. Photographs of anatomy, such as a photograph of a kidney, could be used to train a neural network to display an ultrasound image in the style of the kidney photograph. Alternatively, images obtained with other imaging modalities can be used such as MRI or CT-scan images. Such images may or may not be of the same type of tissue or anatomical feature that is captured in the ultrasound content image 104. In one embodiment, the style image 106 may be another ultrasound image that has been judged to be a good representation of a type of tissue or anatomical feature being examined. Such a designation may be made by expert sonographers or may be an ultrasound image previously captured by the user that has a style that the user likes.

Typically, the neural network 110 is trained remotely on a computer system having more processing power than is available on the ultrasound imaging system. However, if the processing power on the ultrasound imaging system is powerful enough to train a neural network, then the neural network may be trained locally. A processor receives a content image from ultrasound image processing circuitry and trains the neural network to apply a style of a selected style image that may be downloaded from a remote computer system or pre-stored in a memory. In most embodiments, the system is pretrained to apply a particular style to a supplied content image by the training the system on a large number of ultrasound images as content images and using one particular style image. This training allows the neural network to transfer the trained style to new ultrasound images (on which it has not been trained) with a single forward pass of the neural network to achieve real-time style transfer. In other embodiments, the system is trained on the fly from a single content image and style image.

Once the neural network 110 is trained to apply a style to an input image to create a target image in the selected style, the coefficients, weights and bias values determined during the training process are stored locally in a memory of the ultrasound system and used by a processer of the ultrasound imaging system to implement the trained neural network in order to apply the style with which the network is trained to input ultrasound images.

Figure 4:
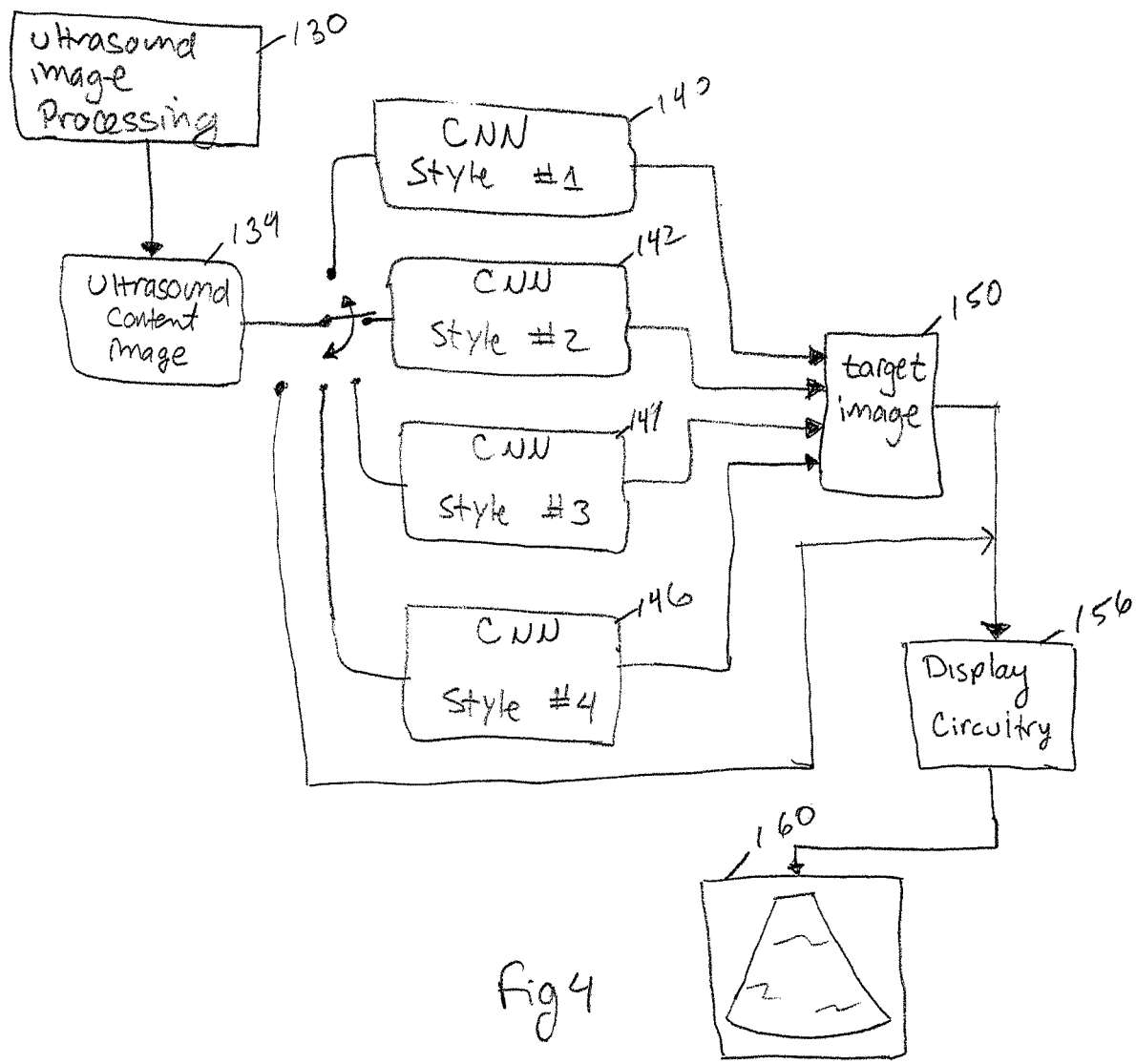
FIG. 4 is a block diagram of a system for applying a selected style to an ultrasound image in accordance with an embodiment of the disclosed technology.

In some embodiments, the ultrasound imaging system stores coefficients, weights and bias values for a number of different neural networks, each of which is trained to apply a different style to an ultrasound image. As shown in FIG. 4, image processing circuitry 130 produces data for an ultrasound image of a region of interest. The data for the ultrasound image are supplied as inputs to one of a number of pre-trained neural networks as a content image 134. In the embodiment shown, the imaging system is configured to implement four trained neural networks 140, 142, 144, 146 that are trained to apply different styles to the supplied content image 134. For example, one neural network 130 may be trained in the style of Gray's Anatomy (pen and ink figures) while another neural network may be trained in the style of anatomical images from a well-known medical textbook or in the style of a photograph of actual organ tissue. One or more neural networks can be trained to apply the style of image obtained with another imaging modality such as MRI or CT-scans. Similarly, a neural network may be trained in the style of an ultrasound image that is deemed by a sonographer or other expert to be a good representation of an anatomical feature such as organ tissue. Such an ultrasound image may have minimal speckle or lack of other artifacts or may have good tissue contrast etc.

In one embodiment, a user views images representative of the styles that each neural network is trained to apply and selects a style image corresponding to the style they would like to apply to the ultrasound image. The processor then selects the corresponding trained neural network associated with the selected style image. In another embodiment, the selected style (and corresponding neural network) may be based on the operating mode of the ultrasound system. For example, when used in a training mode, a style and corresponding trained neural network is selected to mimic color illustrations of anatomy. In another embodiment, the style selected is based on the type of examination being performed or the type of imaging probe being used. For example, the settings for an OB/GYN examination on the ultrasound imaging system can be read by a processor and used to select a style that enhances the look of fetal tissue. Alternatively, if an OB/GYN imaging probe is being used to examine the patient, then the processor may select a style that is appropriate for the types of examination performed with such an imaging probe.

In other embodiments, a past examination history of the patient is used to select the type of style to be applied. For example, the processor in the ultrasound imaging system is programmed to send a message over a wired or wireless communication link to an electronic patient record system to determine the types of prior examinations that the patient has received. If the patient has had an MRI, then an MRI style is selected to be applied to an ultrasound content image. If the patient has had a prior CT-scan, then a CT-scan style can be applied etc.

Once the style to be applied to the ultrasound content image is determined, the processor provides the ultrasound content image 134 as an input to the corresponding trained neural network that produces a target image 150, which combines the content of the content image 104 with the selected style. The target image 150 is provided to display circuitry 156 that shows the image on a display 160 (e.g. one or more video monitors). The target image 150 can also be saved in memory, printed or sent to a remote computer system via a wired or wireless communication link. The content image 134 and the target image 150 can displayed simultaneously (e.g. side by side) or alternatingly.

The style transfer feature is not always used and the processor can provide the ultrasound content image 134 to the display circuitry 156 for display without modification. The user can turn the style transfer feature on and off as desired. In some embodiments, on-board training software executed by the processor may employ the style transfer feature, which is turned off when the user is not using the training software.

As will be appreciated, the ultrasound content image 134 may be image data (e.g. pixel data) that is ready for display on a video monitor. Alternatively, the ultrasound content image may be data that is pre-scanconverted or may be raw RF ultrasound data. Therefore, the term "ultrasound image" that is applied to a neural network as used herein is intended to refer to any ultrasound data received from a patient (human or animal) and not just pixel data that is in a form ready to be displayed.

In some embodiments, the style transfer process is applied to only a portion of an ultrasound content image. In some embodiments, the content image is provided to a neural network (not shown) that is trained to identify types of anatomy or particular organs or other anatomical features in the image. Portions of the image are segmented by the neural network and a selected style is applied to the segmented portion. For example, if liver tissue is identified in an ultrasound image, a section of the image containing the liver tissue is segmented and a style selected to enhance the appearance of liver tissue is applied to the segmented portion. If a blood vessel (e.g. artery, vein) is identified in the image then that portion of the image may be segmented and the same or a different style may be applied to that segment of the image to enhance the appearance of blood in the vessel etc. In this embodiment, two or more different styles may be applied to different segmentations of the image.

In some embodiments, the processor may adjust an amount of style that is applied to the ultrasound content image. For example, the user or software may select to blend less than all of the style of a style image with the content image. Such a reduction may be performed by adjusting the weights, coefficients and bias values used in the trained neural network. In other embodiments, separate neural networks may be trained on different strengths of style transfer for any given style image.

Although the above-disclosed embodiment executes the trained neural network on the ultrasound imaging system, it will be appreciated that the neural network could be implemented on a remote computer system (e.g. cloud computer). In this embodiment, a processor in the ultrasound imaging system is programmed to transmit a content image from the ultrasound imaging system to the remote computer system (and an indication of which style is to be applied if multiple styles are available) via a wired or wireless communication link and to receive a target image in the selected style from the remote computer for display.

Further detail about the functioning of the neural networks (110, 140-146) can be found in 1) Gatys, L. A., Ecker, A. S., Bethge, M.: A neural algorithm of artistic style (2015) and 2) Johnson, J., Alahi, A., Li, F.: Perceptual Losses for Real-Time Style Transfer and Super-Resolution (2016), which are herein incorporated by reference in their entireties.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. An ultrasound imaging system, comprising:
a transducer coupled to the imaging system to deliver ultrasound energy to a region of interest and to detect return echo signals;
a circuitry to process the return echo signals to produce image data for the region of interest; and
a processor; and
a neural network coupled to the processor, wherein the processor is configured to:
generate a content image from the image data;
receive a style image from one or more of style images, wherein the style image is used as a guide to be combined with the content image for displaying on a display device;
supply the content image and the style image to the neural network that is configured to combine the content image with the style image to produce a target image;
calculate a first difference between the target image and the content image and a second difference between the target image and the style image, and feed the first difference and the second difference back to the neural network to lessen the first difference and the second difference; and
display the target image in a style of the style image that retains a content of the content image to enhance the appearance of the content image on the display device.

2. The ultrasound imaging system of claim 1, wherein the processor is configured to:
display a number of the style images on a user interface;
detect a selection of the style image from the number of style images and supply the style image to the neural network associated with the style image that combines the content image with the style image to produce the target image.

3. The ultrasound imaging system of claim 2, wherein the style image is one or more of an anatomical illustration, a previously acquired ultrasound image and a style of another imaging modality.

4. The ultrasound imaging system of claim 1, wherein the processor is configured to select the style image in accordance with an imaging mode of the ultrasound imaging system.

5. The ultrasound imaging system of claim 1, wherein the processor is configured to select the style image in accordance with a type of imaging probe coupled to the ultrasound imaging system.

6. The ultrasound imaging system of claim 1, wherein the neural network coupled to the processor is configured to generate the target image when the ultrasound imaging system operates in a training mode.

7. The ultrasound imaging system of claim 1, wherein the processor is configured to display the content image simultaneously with the target image.

8. The ultrasound imaging system of claim 1, wherein the processor is configured to display the content image alternatingly with the target image.

9. The ultrasound imaging system of claim 1, wherein the neural network coupled to the processor is configured to combine a portion of the content image with the style image.

10. The ultrasound imaging system of claim 9, wherein portions of the content image are combined with different style images.

11. The ultrasound imaging system of claim 9, wherein the neural network coupled to the processor is configured to:
receive the content image;
identify an anatomical feature in the content image;
receive the style image; and
combine the style image with the portion of the content image with the anatomical feature.

12. An ultrasound imaging system comprising:
a processor; and
a plurality of neural networks comprising a first neural network and a second neural network coupled to the processor, wherein the processor is configured to:
receive ultrasound image data of a subject;
receive a content image generated from the image data, wherein the first neural network is trained to apply a first style image to the content image and the second neural network is trained to apply a second style image to the content image, wherein each of the first style image and the second style image used as a guide to be combined with the content image for displaying on a display device;
receive the first style image from one or more of style images;
select the first neural network from the plurality of networks based on the first style image; and
supply the content image to the neural network that is configured to generate a target image by combining the first style image with the content image; and
display the target image in a style of the first style image that retains a content of the content image on the display device.

13. The processor of claim 12, wherein the processor is configured to:
display a number of the style images on a user interface;
detect the selection of the second style image from the number of style images; and
supply the content image to the second neural network to combine with the second style image.

14. The processor of claim 12, wherein the processor is configured to:
determine an imaging mode of the ultrasound imaging system; and
select the first style image in accordance with the determined imaging mode.

15. The processor of claim 12, wherein the processor is configured to: determine a type of imaging probe used to acquire the ultrasound data; and select the first style image in accordance with the type of imaging probe.

16. The processor of claim 12, wherein the processor is configured to:
determine a previous type of examination performed on the subject; and select the first style image based on the type of previous examination.

17. The processor of claim 12, wherein the processor is configured to supply the content image to at least the first neural network and the second neural network to display the target image in at least the style of the first style image that retains the content of the content image and in the style of the second style image that retains the content of the content image.

18. The processor of claim 12, wherein the processor is configured to display the content image of the ultrasound image data and the target image on the display device.

19. The processor of claim 12, wherein the neural network is configured to: identify an anatomical feature in the ultrasound image data; and
combine a portion of the ultrasound image data including the anatomical feature with the first style image.

* * * * *